United States Patent
Campbell et al.

(10) Patent No.: US 10,207,065 B2
(45) Date of Patent: Feb. 19, 2019

(54) MOUTHPIECE FOR INHALERS

(71) Applicants: H. Stuart Campbell, Bear, DE (US);
John H. Silva, Granbury, TX (US)

(72) Inventors: H. Stuart Campbell, Bear, DE (US);
Thomas Shanks, Temecula, CA (US)

(73) Assignees: John H. Silva, Granbury, TX (US); H. Stuart Campbell, Lewes, DE (US)

( * ) Notice: Subject to any disclaimer, the term of this patent is extended or adjusted under 35 U.S.C. 154(b) by 637 days.

(21) Appl. No.: 14/898,195

(22) PCT Filed: Jul. 11, 2014

(86) PCT No.: PCT/US2014/046273
§ 371 (c)(1),
(2) Date: Dec. 14, 2015

(87) PCT Pub. No.: WO2015/006639
PCT Pub. Date: Jan. 15, 2015

(65) Prior Publication Data
US 2016/0144139 A1  May 26, 2016

Related U.S. Application Data

(60) Provisional application No. 61/845,421, filed on Jul. 12, 2013.

(51) Int. Cl.
*A61M 15/00* (2006.01)

(52) U.S. Cl.
CPC ...... *A61M 15/0021* (2014.02); *A61M 15/009* (2013.01); *A61M 15/0086* (2013.01)

(58) Field of Classification Search
CPC .. A61M 11/00; A61M 15/00; A61M 15/0001; A61M 15/0021; A61M 15/0025;
(Continued)

(56) References Cited

U.S. PATENT DOCUMENTS 3,548,823 A  12/1970 Bogacik
3,809,294 A  5/1974 Torgeson
(Continued)

FOREIGN PATENT DOCUMENTS

TW  201408340 A  3/2014
TW  201410278 A  3/2014
(Continued)

OTHER PUBLICATIONS

Office Action dated Feb. 19, 2016 in TW Application No. 103123962.
(Continued)

*Primary Examiner* — (Jackie) Tan-Uyen T Ho
*Assistant Examiner* — Joseph D Boecker
(74) *Attorney, Agent, or Firm* — Rogowski Law LLC

(57) ABSTRACT

A mouthpiece (10) for an inhaler or inhalation device (100) includes an elongated body (12) having a substantially oval opening (14) at a first end and a substantially round opening (18) at a second end opposite from the first end, a plurality of depending arms (24), extending from the elongated body forming at least one air passageway (26) between two depending arms (24), and at least one flexible gripping finger (32) coupled to an inner surface of each depending arm (24), extending inwardly into the medicament delivery passageway of the mouthpiece at or near the substantially round opening (18) at the opposite end. Once coupled with an inhaler or inhalation device, the mouthpiece functions as a "pass through" mouthpiece to improve the consistency of inhaled medicament/drug delivery.

16 Claims, 5 Drawing Sheets

(58) Field of Classification Search
CPC .......... A61M 15/0026; A61M 15/0086; A61M 15/0088; A61M 15/009; A61M 16/0488; A61M 16/049; A62B 9/06; A24D 3/00; A24D 3/18; A61C 5/90; A61C 19/063; A24C 5/47; A24C 5/476; A61D 15/00
See application file for complete search history.

(56) References Cited

U.S. PATENT DOCUMENTS

| | | | |
|---|---|---|---|
| 3,856,185 A | 12/1974 | Riccio | |
| 3,906,950 A | 9/1975 | Cocozza | |
| 3,991,761 A * | 11/1976 | Cocozza | A61M 15/0028 128/203.15 |
| 3,998,226 A | 12/1976 | Harris | |
| 4,013,075 A | 3/1977 | Cocozza | |
| 4,227,522 A | 10/1980 | Carris | |
| 4,456,007 A | 6/1984 | Nakao et al. | |
| 4,484,577 A * | 11/1984 | Sackner | A61K 9/0073 128/200.23 |
| 4,706,663 A | 11/1987 | Makiej | |
| 5,007,419 A | 4/1991 | Weinstein et al. | |
| D335,343 S | 5/1993 | Jones et al. | |
| 5,477,849 A | 12/1995 | Fry | |
| 5,505,194 A * | 4/1996 | Adjei | A61M 15/0086 128/200.23 |
| 5,598,836 A * | 2/1997 | Larson | A61M 15/0086 128/200.14 |
| 5,848,588 A | 12/1998 | Foley et al. | |
| 5,855,202 A | 1/1999 | Andrade | |
| D412,979 S | 8/1999 | Weinstein et al. | |
| 6,039,042 A | 3/2000 | Sladek | |
| D441,069 S | 4/2001 | Hammarlund et al. | |
| D442,685 S | 5/2001 | Sladek | |
| 6,293,279 B1 | 9/2001 | Schmidt et al. | |
| 6,345,617 B1 | 2/2002 | Engelbreth et al. | |
| 6,418,925 B1 * | 7/2002 | Genova | A61M 15/009 128/200.14 |
| 6,435,176 B1 | 8/2002 | Berg et al. | |
| D463,544 S | 9/2002 | Engelbreth et al. | |
| D476,413 S | 6/2003 | Pearce, Jr. et al. | |
| D480,138 S | 9/2003 | Engelbreth et al. | |
| D480,806 S | 10/2003 | Engelbreth et al. | |
| 6,679,252 B2 | 1/2004 | Sladek | |
| 6,962,152 B1 | 11/2005 | Sladek | |
| 7,178,518 B2 | 2/2007 | Watt et al. | |
| D574,951 S | 8/2008 | Reusch | |
| 7,418,962 B1 | 9/2008 | Rao | |
| D583,929 S | 12/2008 | Reusch | |
| D697,200 S | 1/2014 | Mahaffy | |
| D805,629 S * | 12/2017 | Fiorenza | D24/110 |
| 2002/0026935 A1 * | 3/2002 | Schmidt | A61M 15/0086 128/200.14 |
| 2002/0029779 A1 | 3/2002 | Schmidt et al. | |
| 2002/0121276 A1 * | 9/2002 | Genova | A61M 15/0086 128/200.23 |
| 2003/0197068 A1 | 10/2003 | Abate | |
| 2003/0205226 A1 * | 11/2003 | Gallem | A61M 15/0086 128/200.14 |
| 2005/0081845 A1 | 4/2005 | Barney et al. | |
| 2005/0126561 A1 | 6/2005 | Glychowski et al. | |
| 2006/0169280 A1 * | 8/2006 | Yama | A61M 15/0028 128/203.21 |
| 2006/0269484 A1 * | 11/2006 | Knopeck | A61K 31/44 424/45 |
| 2007/0277821 A1 * | 12/2007 | Oliva | A61M 15/0028 128/203.15 |
| 2008/0078383 A1 | 4/2008 | Richards et al. | |
| 2009/0071470 A1 | 3/2009 | Abrams | |
| 2009/0071473 A1 | 3/2009 | Abrams | |
| 2009/0151716 A1 | 6/2009 | Abrams | |
| 2009/0308390 A1 | 12/2009 | Smutney et al. | |
| 2010/0269818 A1 | 10/2010 | Abrams | |
| 2011/0180067 A1 | 7/2011 | Avni | |
| 2011/0226242 A1 | 9/2011 | Von Hollen et al. | |
| 2011/0232636 A1 * | 9/2011 | Von Hollen | A61M 15/0086 128/202.13 |
| 2011/0283996 A1 | 11/2011 | Abrams | |
| 2012/0042874 A1 | 2/2012 | Gallem et al. | |
| 2012/0160241 A1 | 6/2012 | Oliva | |
| 2013/0186393 A1 * | 7/2013 | Von Hollen | A61M 15/0086 128/200.23 |
| 2013/0213397 A1 * | 8/2013 | Curtis | A61M 15/0045 128/203.15 |
| 2013/0233313 A1 | 9/2013 | Young et al. | |
| 2013/0276781 A1 * | 10/2013 | Steelman | A61M 15/0086 128/203.12 |
| 2013/0291862 A1 * | 11/2013 | Eagle | A61M 15/0086 128/203.12 |
| 2014/0096770 A1 | 4/2014 | Neff et al. | |
| 2014/0116426 A1 | 5/2014 | Mullinger et al. | |
| 2014/0251321 A1 * | 9/2014 | Benson | A61M 15/009 128/200.23 |

FOREIGN PATENT DOCUMENTS

| | | |
|---|---|---|
| WO | 2006059340 A1 | 6/2006 |
| WO | 2010070053 A1 | 6/2010 |

OTHER PUBLICATIONS

Int'l Preliminary Report on Patentability and Written Opinion dated Jan. 12, 2016 in Int'l Application No. PCT/US2014/046273.
International Search Report dated Oct. 17, 2014 in International Application No. PCT/US2014/046273.
Nikander, et al., "The Evolution of Spacers and Valved Holding Chambers", Journal of Aerosol Medicine and Pulmonary Drug Delivery, vol. 27, Supp. 1, (2014).

* cited by examiner

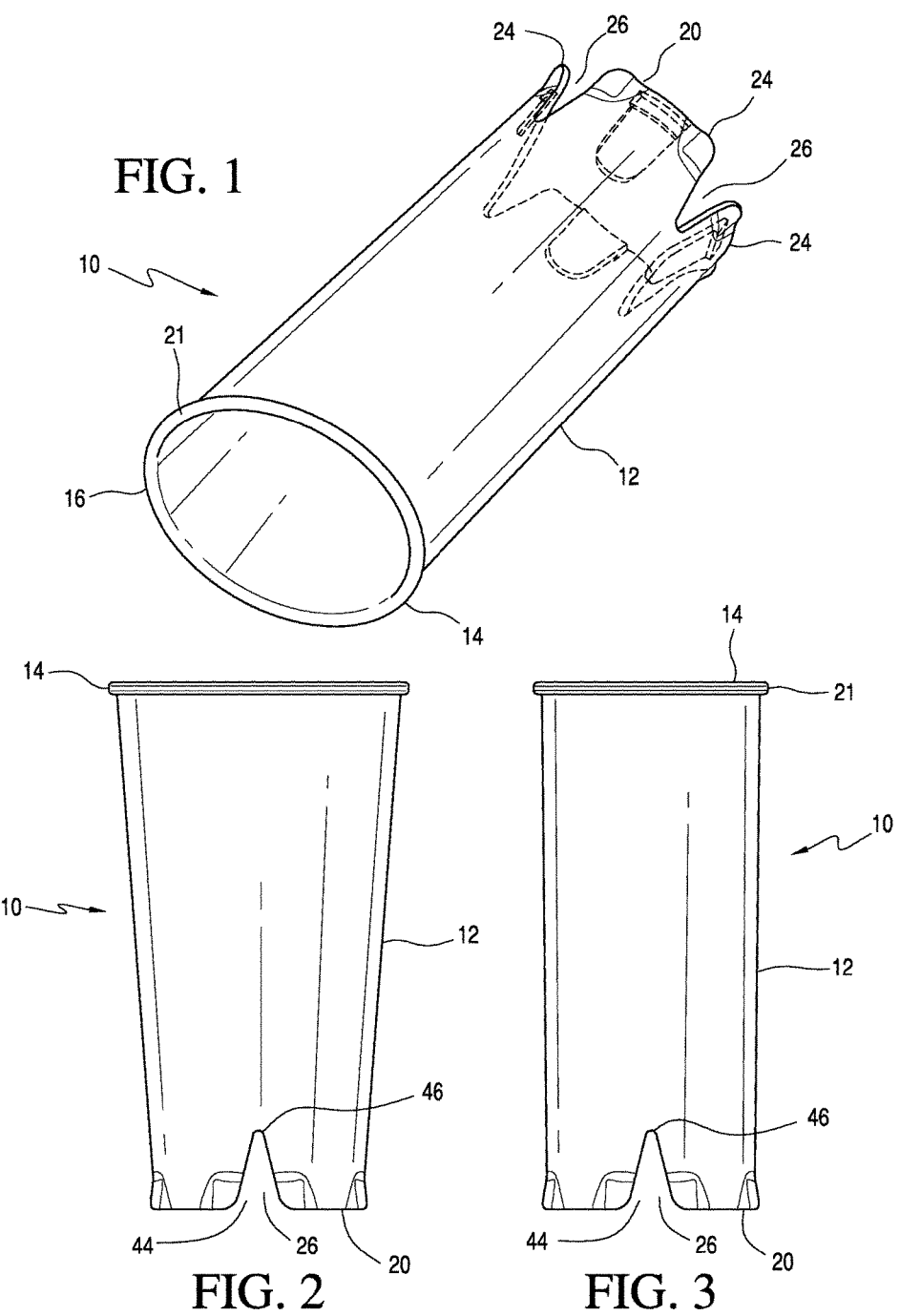

MOUTHPIECE FOR INHALERS

CROSS-REFERENCE TO RELATED APPLICATIONS

This application is a national stage application (under 35 USC § 371) of PCT/US2014/046273, filed Jul. 11, 2014, which claims priority to U.S. Patent Application Ser. No. 61/845,421, filed Jul. 12, 2013, the entirety of which is incorporated herein by reference.

BACKGROUND

The present disclosure relates to mouthpieces configured for use with inhalers.

Asthma patients administer bronchodilators and glucocorticosteroids with inhalation devices or inhalers. Effective inhalation devices produce an aerosol of medication with a significant dose of particles in the so-called respirable range that enters the lower airways. Inhalation devices generally include a canister that holds medicament under pressure and a boot portion in which the canister is seated. The boot portion includes a mechanism, which causes the canister to release some of the medicament in aerosol form.

Metered-dose inhalers (MDIs) and pressurized metered-dose inhalers (pMDIs) are widely used by asthma patients. Nonetheless, even when these types of inhalers are used correctly, only about 10% to 20% of the nominal per puff dose reaches targeted airways. Due to the rate and pressure at which medicament is expelled from an MDI or pMDI, much of the medicament impinges upon oral and throat tissues and does not reach the patient's lungs, as intended.

Various techniques have been proposed in an effort to improve inhaled drug delivery. One technique, termed the "open-mouth" technique, positions an egress opening of the MDI or pMDI about 2 inches from the patient's mouth. The medicament is then sprayed directly into the patient's open mouth while the patient inhales deeply and slowly. With the open-mouth technique, the medicament enters the patient's mouth and lungs at a slower rate and under less pressure, so that more medicament reaches the deep lungs. The open-mouth technique, however, is often not recommended by medical practitioners. Frequently, patients who attempt this technique fail to achieve consistent, repeatable and successful dosing. Many patients, for example, mis-aim the inhaler or inhale too quickly.

In some cases, a spacing device or holding chamber is combined with the MDI or pMDI to slow the velocity of the aerosol and allow more time for the propellant to evaporate. Some spacing devices hold the medicament aerosol discharged from the pMDI in suspension for approximately 2-3 seconds, which allows the patient to inhale more medicament at a slower rate. Unfortunately, some patients using spacing devices continue to experience problems, such as failing to receive sufficient medicament dosage because the patient has inhaled before actuating the pMDI, or waiting too long after actuation before inhaling.

Solutions to problems associated with inhalation devices and ineffective inhaled drug delivery continue to be sought.

SUMMARY OF THE INVENTION

The present invention relates to mouthpieces for inhalers or inhalation devices. One mouthpiece embodiment includes an elongated body defining a medicament delivery passageway and having a substantially oval opening at a first end and a substantially round opening a second end, opposite from the first end. The mouthpiece further includes a plurality of depending arms, extending from the elongated body, which form at least one air passageway between two depending arms, and at least one flexible gripping finger coupled to an inner surface of each depending arm, extending toward an internal surface of the mouthpiece at or near the substantially round opening at the opposite end. Once coupled with the inhaler or inhalation device, the mouthpiece functions as a "pass through" mouthpiece to improve the consistency and repeatability of inhaled medicament/drug delivery. One expected benefit of the mouthpiece embodiments described herein include the prevention of spraying in a user's face, which reduces potential medicament/drug side effects and provides slower medicament/drug delivery.

BRIEF DESCRIPTION OF THE SEVERAL VIEWS OF THE DRAWINGS

The drawings herein are for illustrative purposes only and are not intended to limit the scope of the present disclosure. In the drawings:

FIG. 1 is a right front perspective view of one embodiment of a mouthpiece configured for removable attachment to a boot portion of an inhaler or inhalation device;

FIG. 2 is a front elevational view of the mouthpiece of FIG. 1 with the mouthpiece placed in an upright position;

FIG. 3 is a right side elevational view of the mouthpiece shown in FIG. 2;

DETAILED DESCRIPTION

Figure 4:
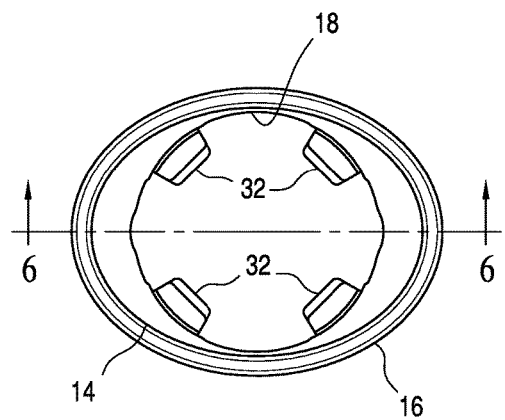
FIG. 4 is a top plan view of the mouthpiece shown in FIG. 2.

Turning in detail to the drawings, FIGS. 1-11 show one embodiment of a mouthpiece 10 that may be coupled with various types of inhalers or inhalation devices. Exemplary inhalers or inhalation devices include, but are not limited to metered-dose inhalers (MDIs) and pressurized metered-dose inhalers (pMDIs).

As particularly shown in FIG. 1, the mouthpiece generally has a cone-like shape. The mouthpiece 10 includes an elongated body 12 defining an internal medicament delivery passageway. The elongated body 12 has a substantially oval opening 14 at a first end 16 and a substantially round opening 18 (FIG. 4) at a second end 20, which is opposite from the first end. The elongated body 12 is formed to have a substantially uniform wall 22 (FIG. 6) that tapers inwardly from the first end 18 to the second end 20. The mouthpiece is configured so that the substantially round opening may be removably attached to boot portions of various MDI or pMDI, interchangeably. Thus, users are not restricted to one style of MDI or pMDI, and may use the mouthpiece of this embodiment of the invention more universally with various MDI or pMDI.

The first end 16 of the mouthpiece 10 preferably includes a lip-engaging rim 21, which is integral with the elongated body 12. The lip-engaging rim 21 may be provided at or near the edge of the substantially oval opening of the mouthpiece at the first end 16. During use, a patient may elect to engage the rim 21 with his or her teeth in addition to his or her lips to ensure his or her mouth is sufficiently open to receive the inhaled medicament.

The second end 20 of the mouthpiece 10 includes a plurality of depending arms 24 with notched or v-shaped air flow passageways 26 formed between each arm 24. One preferred configuration includes four depending arms 24. Different mouthpiece embodiments may, however, incorporate fewer or additional arms.

Figure 6:
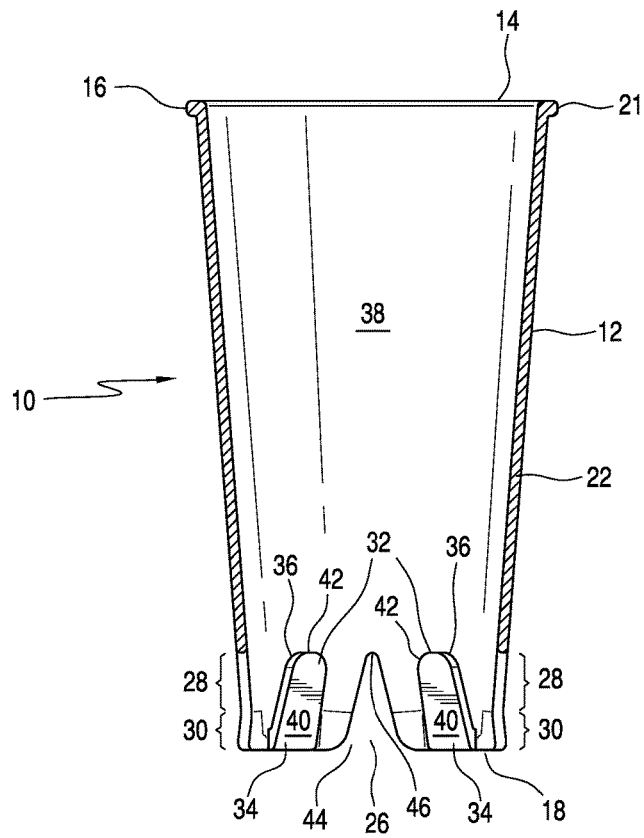
FIG. 6 is a cross-sectional view taken along line 6-6 in FIG. 4.
Figure 7:
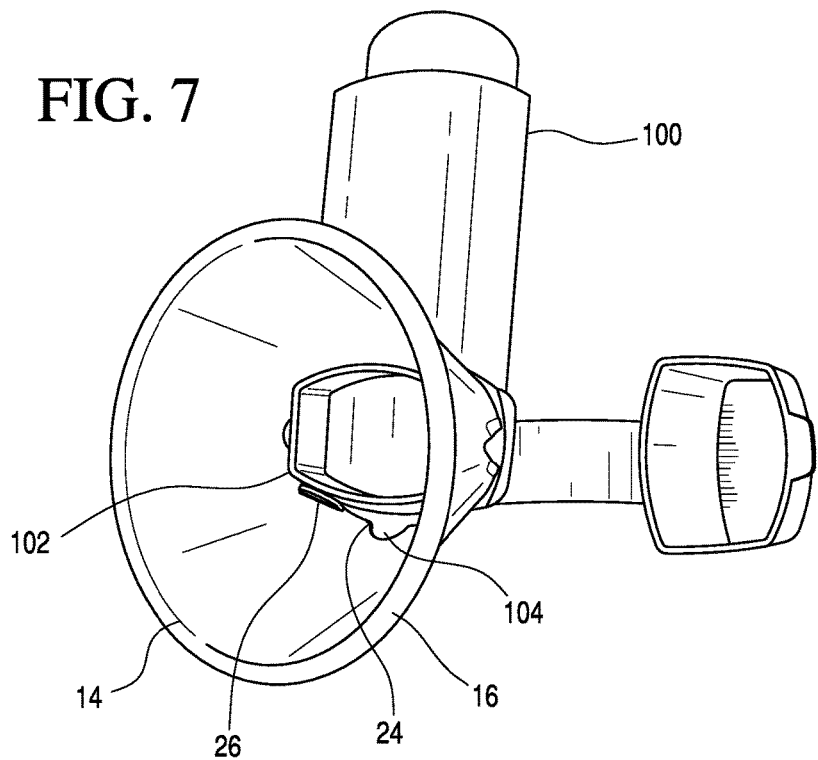
FIGS. 7 and 8 show the mouthpiece engaged to the boot portion of one type of inhaler or inhalation device.
Figure 8:
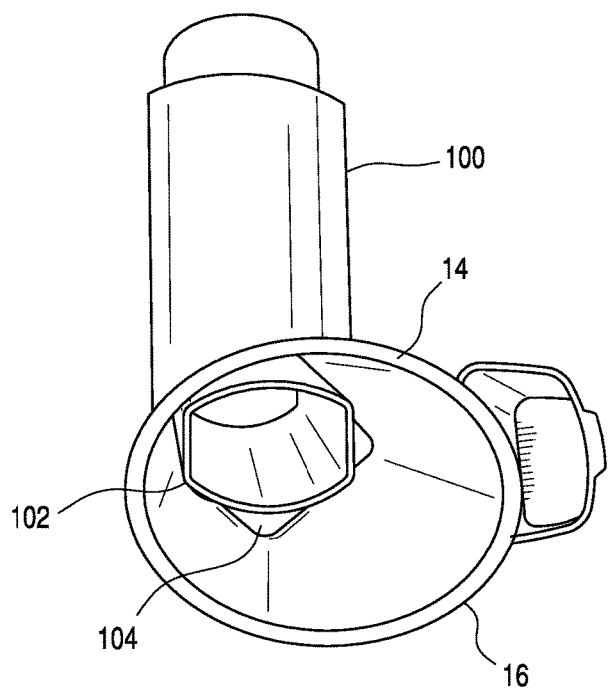
Figure 9:
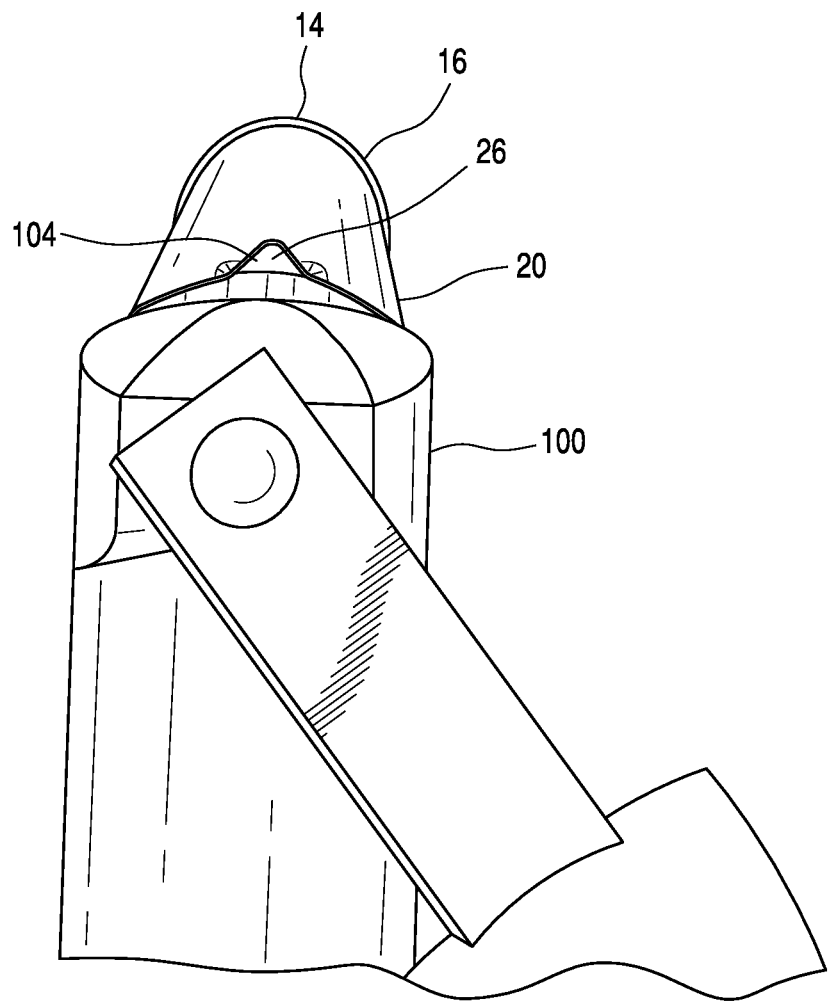
FIG. 9 shows the mouthpiece engaged to a boot portion of an inhaler, as viewed from the rear of the inhaler, wherein one of the air flow spaces between the inhaler boot and the mouthpiece is more distinctly shown.

As shown particularly in FIG. 6, each depending arm 24 includes an upper arm portion 28 and a lower arm portion 30. Each upper arm portion 28 is formed to continue the taper of the wall 22 of the elongated body 12, while each lower arm portion 30 extends slightly outwardly at an angle with respect to the most inwardly tapered end of the elongated body 12.

Figure 5:
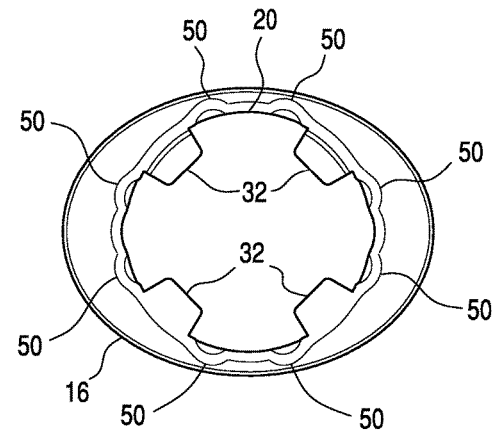
FIG. 5 is a bottom plan view of the mouthpiece shown in FIG. 2.

Coupled to the inner surface of each depending arm 24 and preferably at or near the lower arm portion 30 is a flexible gripping finger 32. Each gripping finger 32 extends at an angle toward the inner center or internal medicament delivery passageway of the mouthpiece 10, as shown in FIGS. 4 and 5, at the second end 20. The flexible gripping fingers 32 are intended for contact with a boot or an egress opening of an inhaler or inhalation device. Together a plurality of the gripping fingers 32 acts to hold the mouthpiece in place on the inhaler or inhalation device.

Still referring to FIG. 6, each flexible gripping finger 32 includes a bottom end 34, terminating at or near the substantially round opening 18 at the opposite end 20 of the cone-shaped mouthpiece 10 and a tip end 36 spaced apart from the internal surface 38 of the mouthpiece 10. Each of the plurality of flexible gripping fingers 32 is spaced apart from another of the plurality of the flexible gripping fingers in an array formed around the internal surface 38 at or near the substantially round opening 18 at the opposite end 20 of the mouthpiece 10.

The gripping fingers 32 in the embodiment shown in FIG. 6 include curved faces 40 that generally follow the curvature of the cone-shaped mouthpiece 10 at the substantially round opening 18. For example, the radius of curvature may be about 30 degrees for the face of each gripping finger 32. In a preferred embodiment, each flexible gripping finger 32 has a tip end with a rounded upper edge 42. In one preferred embodiment, each flexible gripping finger 32 is formed integrally with the material forming the mouthpiece 10.

The notched or v-shaped air flow passages 26 in the embodiment shown in FIG. 6 are formed between the flexible gripping fingers 32 in an array. The v-shaped air flow passages 26 have sufficient gap between the mouthpiece 10 and the inhaler or inhalation device such that room air may be drawn into the internal medicament delivery passageway of the mouthpiece 10. In one embodiment, the mouthpiece 10 defines at least one v-shaped air flow passage 26 at the substantially round opening. The v-shaped air flow passage 26 has its widest opening 44 at the substantially round opening 18 at the second end 20 of the mouthpiece 10 and terminates at a tip end 46. Preferably, the at least one air flow passage 26 is spaced between two of the plurality of flexible gripping fingers 32. Where more than one air flow passage is provided, the air flow passages 26 may be disposed in a spaced-apart array around the substantially round opening 18, with each air flow passage 26 positioned between a pair of flexible gripping fingers 32.

The mouthpiece 10 may be sized differently, depending on the type of inhaler or inhalation device with which it is intended to be used. Preferably, the mouthpiece is sized to have a universal fit with a variety of different inhalers and inhalation devices. According to one embodiment, the mouthpiece has a length, measured from the first end 16 to the opposite second end 20 of from about 50 mm to about 85 mm. The diameter of the substantially round opening 18 at the opposite end 20 in this same embodiment ranges from about 20 mm to about 28 mm, and preferably from about 24 mm to about 26 mm. The outer diameter of the substantially oval opening 14 at the first end 16 at its widest dimension is from 35 to 50 mm, preferably 38 to 40 mm, and the outer diameter of the substantially oval opening 14 at the first end 16 at its narrowest opening dimension ranges from about 25 mm to about 40 mm, and preferably from about 28 to about 32 mm. The thickness of the sidewall of the elongated body of the mouthpiece 10 ranges from about 0.8 mm to about 2 mm, and preferably from about 1.0 mm. The length of each flexible gripping finger 32 preferably ranges from about 6 mm to about 15 mm, and more preferably from about 8 mm to about 10 mm. The thickness of each flexible gripping finger 32 preferably ranges from about 0.75 mm to about 0.92 mm, and most preferably from about 0.89 mm to about 0.9 mm In this embodiment, the air flow passageway 26 has a passage length of about 10 mm and the passage opening ranges from about 25 to 30 degrees, and preferably is 28 degrees. Also in the embodiment shown, the depending arms 24 each have a length, and the air flow passages 26 each have a length substantially equal to the length of at least one of the plurality of arms 24.

FIGS. 7-11 show various views of the mouthpiece 10 coupled to an inhaler or inhalation device 100. Once coupled with a boot portion 102 of the device 100, the mouthpiece functions as a "pass through" mouthpiece to improve the consistency of inhaled medicament/drug delivery. During use, there are at least some portions of the internal wall of the mouthpiece 10, which are separated from or spaced apart from external surfaces of the boot portion 102 of the inhalation device 100, as particularly shown in FIGS. 7-11. As a result, air may flow between the mouthpiece 10 and the boot portion 102 of the inhalation device 100. The air flow spaces may be between the flexible gripping fingers. Alternatively, or in addition, the air flow spaces 104 may be positioned between the depending arms 24 and/or the gripping fingers 32.

Alternatively, or in addition, as shown in FIG. 5, the substantially round opening 18 at the opposite second end 20 of the mouthpiece 10 includes outwardly directed bends 50 in the material forming the mouthpiece. The outwardly directed bends 50 at this end of the mouthpiece also create air flow spaces between the boot portion of the inhaler or inhalation device and the mouthpiece 10 to permit air flow between the inner sidewall of the mouthpiece and the outer surface of the boot of the inhaler.

Figure 10:
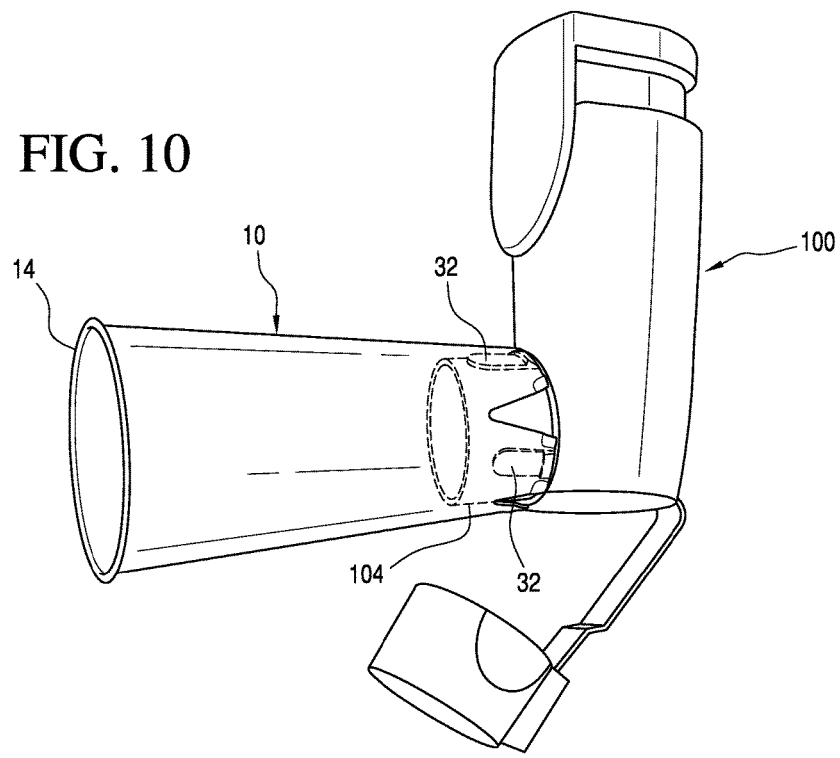
FIGS. 10 and 11, respectively, show the mouthpiece engaged in a first configuration and a second configuration 90 degrees turned from the first configuration, wherein air flow spaces between the boot portion of the inhaler and the mouthpiece are distinctly shown.
Figure 11:
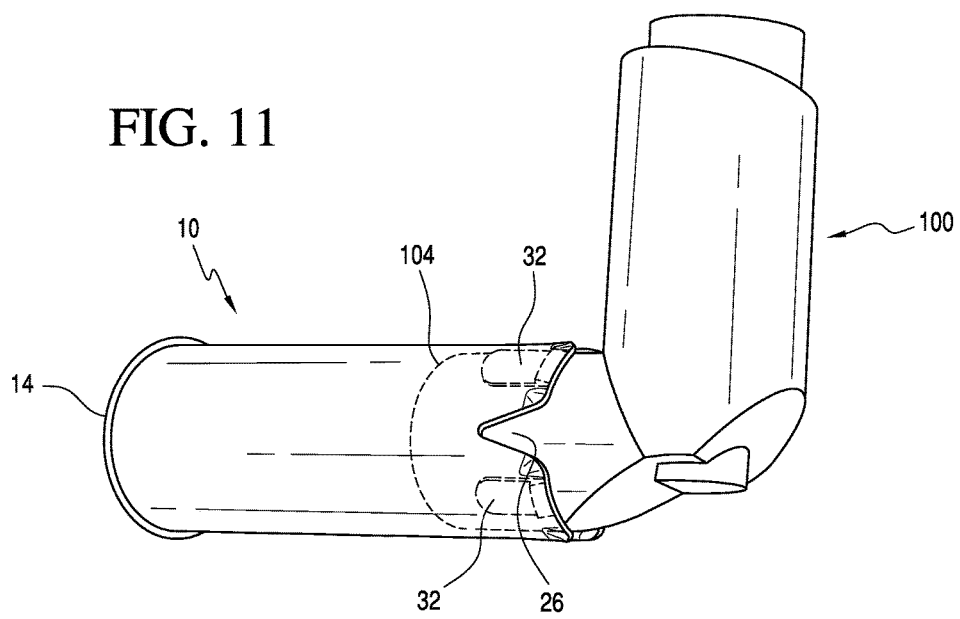

Referring to FIGS. 10 and 11, the mouthpiece 10 may be attached to an inhaler or inhalation device 100 in at least two configurations. According to a first configuration, shown in FIG. 10, the mouthpiece 10 may be attached to an inhalation device, wherein the oval opening 14 of the mouthpiece 10 is oriented in a "vertical" position, with the larger diameter of the substantially oval opening being perpendicular to a horizontal axis. Alternatively, according to a second configuration shown in FIG. 11, the oval opening 14 of the mouthpiece 10 may be oriented in a "horizontal" position, with the larger diameter of the substantially oval opening being parallel to a horizontal axis. The second configuration has the mouthpiece 10 rotated 90 degrees from the first configuration. Thus, patients may select whether it is more comfortable for them to use the mouthpiece in the first configuration or second configuration.

The mouthpiece 10 for an inhalation device may be formed from one or more mouldable polymeric materials. Representative polymeric materials include: polypropylene, ethylene methyl acrylate (EMA) copolymers, acrylics, high density polyethylenes (HDPE), styrenics (IMPS), acrylonitrile-butadiene-styrene (ABS) copolymers, poly(methylmethacrylates) polycarbonate, polycaprolactam, polycaprolactone, polyurethanes, polyesters, polypropylene-ethylene propylene diene monomer (PP/EPDM), thermoplastic vulcanizates (TPV), acrylic rubber TPV, styrene-butadiene-styrene (SBS) TPV, low density polyethylene (LDPE), polyvinylchoride (PVC), very low density polyethylene (VLDPE), styrene-butadiene copolymer (SBC) elastomer compounds, styrene-butadiene-styrene (SBS) linear block copolymers, styrene-isoprene-styrene (SIS) linear block copolymers, styrene-butadiene (SB)n branched copolymers, styrene-co-ethylene-butene-styrene (SEBS) linear block copolymers, styrene-co-ethylene-propylene (SEP) diblock copolymers, styrene-co-ethylene-ethylene-propylene-styrene (SEEPS) copolymers, mineral reinforced thermoplastic ethylene-styrene (TES/SEBS), polyethersulfone (PES), glass reinforced polyethersulfone, polyphenylsulfone (PPSU), styrene-acrylonitrile (SAN), acrylic-styrene-methylmethacrylate coploymers (NAS), polydimethylsilicone (PDMS), polyurea, silicone-polyurea, segmented polyurethane (SPU), perfluoroelastomer (FFKM), perfluoroelastomer (FEPM), chlorosulfonated polyethylene rubber, fluoroelastomer, silicone room temperature vulcanizate (RTV), cast polyurethane, chloroprene rubber, hydrogenated nitrile-butadiene rubber (HNBR), nitrile rubber, silicone rubber, perfluoroelastomer compounds (FFKT), and mixtures thereof.

The mouthpiece 10 for an inhaler or inhalation device also may be formed from molded fibrous wood pulp, which is optionally combined with other fibers. Films, such as polyester films, may be further be applied to wood pulp/fiber molded surfaces.

Optionally, a logo or other indicia or advertising message may be displayed on the external surface of the cone-shaped mouthpiece.

Thus, various embodiments and configurations of mouthpieces for inhalers or inhalation devices are disclosed herein. While embodiments of this invention have been shown and described, it will be apparent to those skilled in the art that many more modifications are possible without departing from the inventive concepts herein. The invention, therefore, is not to be restricted except in the spirit of the following claims.

We claim:

1. A mouthpiece (10) for an inhalation device having an elongated body (12) defining a medicament delivery passageway, said elongated body having a substantially oval opening (14) at a first end (16) and a substantially round opening (18) at a second end (20) opposite from the first end, characterized in that:
a plurality of depending arms (24) extends from the elongated body and forms at least one air flow passageway (26) between two depending arms that is adapted for air flow into the medicament delivery passageway; and in that
at least one flexible gripping finger (32) is coupled to an inner surface of each depending arm (24) and extends inwardly into the medicament delivery passageway of the mouthpiece at or near the substantially round opening (18).

2. The mouthpiece for an inhalation device of claim 1, wherein the elongated body (12) has a substantially uniform wall.

3. The mouthpiece for an inhalation device of claim 1, wherein the at least one air flow passageway (26) has a v-shape.

4. The mouthpiece for an inhalation device of claim 3, wherein the at least one air flow passageway (26) has its widest opening at the substantially round opening (18) at the opposite end (20) of the mouthpiece (10) and terminates at a tip end.

5. The mouthpiece for an inhalation device of claim 1, further comprising a lip-engaging rim (21) formed at the first end (16).

6. The mouthpiece for an inhalation device of claim 2, wherein each depending arm (24) includes an upper arm portion (28) and a lower arm portion (30).

7. The mouthpiece for an inhalation device of claim 6, wherein the lower arm portion (30) extends outwardly at an angle with respect to a most inwardly tapered end of the elongated body (12).

8. The mouthpiece for an inhalation device of claim 1, wherein each flexible gripping finger (32) is formed integrally with the material forming the mouthpiece.

9. The mouthpiece for an inhalation device of claim 1, wherein each flexible gripping finger (32) has a bottom end (34) terminating at or near the substantially round opening (18) at the opposite end of the elongated body (12), and a tip end (42) spaced apart from an internal surface of the elongated body (12).

10. The mouthpiece for an inhalation device of claim 1, wherein each flexible gripping finger (32) is spaced apart from another of the plurality of the flexible gripping fingers in an array around an internal surface at or near the substantially round opening (18) at the opposite end of the elongated body (12).

11. The mouthpiece for an inhalation device of claim 1, wherein each flexible gripping finger (32) has a tip end (42) with a rounded upper edge.

12. The mouthpiece for an inhalation device of claim 1, wherein the mouthpiece is formed from at least one moldable polymeric material selected from the group consisting of: polypropylene, ethylene methyl acrylate (EMA) copolymers, acrylics, high density polyethylenes (HDPE), styrenics (IMPS), acrylonitrile-butadiene-styrene (ABS) copolymers, poly(methylmethacrylates) (IM-PMMA), polycarbonate, polycaprolactam, polycaprolactone, polyurethanes, polyesters, polypropylene-ethylene propylene diene monomer (PP/EPDM), thermoplastic vulcanizates (TPV), acrylic rubber TPV, styrene-butadiene-styrene (SBS) TPV, low density polyethylene (LDPE), polyvinylchoride (PVC), very low density polyethylene (VLDPE), styrene-butadiene copolymer (SBC) elastomer compounds, styrene-butadiene-styrene (SBS) linear block copolymers, styrene-isoprene-styrene (SIS) linear block copolymers, styrene-butadiene (SB)n branched copolymers, styrene-co-ethylene-butene-styrene (SEBS) linear block copolymers, styrene-co-ethylene-propylene (SEP) diblock copolymers, styrene-co-ethylene-ethylene-propylene-styrene (SEEPS) copolymers, mineral reinforced thermoplastic ethylene-styrene (TES/SEBS), polyethersulfone (PES), glass reinforced polyethersulfone, polyphenylsulfone (PPSU), styrene-acrylonitrile (SAN), acrylic-styrene-methylmethacrylate coploymers (NAS), polydimethylsilicone (PDMS), polyurea, silicone-polyurea, segmented polyurethane (SPU), perfluoroelastomer (FFKM), perfluoroelastomer (FEPM), chlorosulfonated polyethylene rubber, fluoroelastomer, silicone room temperature vulcanizate (RTV), cast polyurethane, chloroprene rubber, hydrogenated nitrile-butadiene rubber (HNBR), nitrile rubber, silicone rubber, perfluoroelastomer compounds (FFKT), and mixtures thereof.

13. The mouthpiece for an inhalation device of claim 1, wherein the mouthpiece is formed from a molded fibrous wood pulp or wood pulp mixed with other fibers.

14. A method for inhaling a medicament, comprising:

applying a mouthpiece (10), as claimed in claim 1, to an inhalation device (100), wherein said one or more air flow passageways (26) are established between the plurality of depending arms (24) so that air may flow into the medicament delivery passageway of the mouthpiece (10) through said one or more air flow passageways (26);

activating the inhalation device to release medicament into the medicament delivery passageway of the mouthpiece; and inhaling the medicament through the mouthpiece.

15. The method of claim 14, wherein portions of the depending arms (24) that define the one or more air flow passageways (26) extend outwardly away from a center axis of the elongated body (12) so that air flows into the medicament delivery mouthpiece passageway and the inhalation device.

16. An inhalation device kit, comprising:

a mouthpiece, as claimed in claim 1; and an inhalation device having a boot portion, wherein the mouthpiece is configured to removably couple with the boot portion such that air flow spaces are formed between the mouthpiece and external surfaces of the boot portion to permit air flow into the medicament delivery passageway of the mouthpiece.

* * * * *